United States Patent
Irick et al.

(10) Patent No.: US 7,278,186 B2
(45) Date of Patent: Oct. 9, 2007

(54) ULTRA LOW FREQUENCY MOISTURE SENSOR

(75) Inventors: Glenn E. Irick, Maynardville, TN (US); Michael E. Galyon, Knoxville, TN (US); Hossein M. Ghorashi, Knoxville, TN (US)

(73) Assignee: Uster Technologies AG, Uster (CH)

( * ) Notice: Subject to any disclaimer, the term of this patent is extended or adjusted under 35 U.S.C. 154(b) by 526 days.

(21) Appl. No.: 11/029,272

(22) Filed: Jan. 5, 2005

(65) Prior Publication Data

US 2006/0143870 A1 Jul. 6, 2006

(51) Int. Cl.
*G01B 15/00* (2006.01)
(52) U.S. Cl. .................................. 19/66 CC
(58) Field of Classification Search ............. 19/66 CC; 73/73, 74
See application file for complete search history.

(56) References Cited

U.S. PATENT DOCUMENTS

| | | | | |
|---|---|---|---|---|
| 4,156,843 A | | 5/1979 | Strandberg, Jr. et al. ... | 324/643 |
| 4,361,801 A | | 11/1982 | Meyer et al. ............... | 324/638 |
| 4,616,425 A | * | 10/1986 | Burns ........................ | 34/389 |
| 5,418,466 A | | 5/1995 | Watson et al. ............... | 324/668 |
| 5,483,172 A | | 1/1996 | Radford ..................... | 324/693 |
| 5,514,973 A | | 5/1996 | Byler et al. ................. | 324/695 |
| 5,621,330 A | | 4/1997 | Greenwald et al. ......... | 324/640 |
| 5,838,158 A | | 11/1998 | Beck et al. ................. | 324/636 |
| 6,025,724 A | | 2/2000 | Moshe et al. .............. | 324/640 |
| 6,107,809 A | | 8/2000 | Moshe et al. .............. | 324/640 |
| 6,111,415 A | | 8/2000 | Moshe ........................ | 324/640 |
| 6,121,782 A | | 9/2000 | Adams et al. .............. | 324/689 |
| 6,134,953 A | * | 10/2000 | Verheecke ................... | 73/73 |
| 6,204,670 B1 | | 3/2001 | Joshi .......................... | 324/643 |
| 6,242,927 B1 | | 6/2001 | Adams et al. .............. | 324/664 |
| 6,275,046 B1 | | 8/2001 | Moffett et al. ............... | 324/640 |
| 6,278,412 B1 | | 8/2001 | Kelly et al. ................. | 343/786 |
| 6,346,819 B1 | | 2/2002 | Joss et al. ................... | 324/665 |
| 6,407,555 B2 | | 6/2002 | Joshi et al. ................. | 324/636 |
| 6,411,106 B1 | | 6/2002 | Holmes et al. ............. | 324/643 |
| 6,476,619 B1 | | 11/2002 | Moshe et al. .............. | 324/634 |
| 6,489,784 B2 | | 12/2002 | Adams et al. .............. | 324/664 |
| 6,669,557 B2 | | 12/2003 | Adams et al. ............... | 460/7 |

* cited by examiner

*Primary Examiner*—Shaun R. Hurley
(74) *Attorney, Agent, or Firm*—Luedeka, Neely & Graham, P.C.

(57) ABSTRACT

An apparatus for measuring a moisture content value within a volume. A frequency generator generates at least one source signal at frequencies of no more than about one kilohertz. Probes are disposed with surfaces in physical contact with the volume, where no direct current flows between the probes through the volume. One of the probes is electrically connected to the frequency generator as a source probe, and adapted to receive the source signal and emit the source signal into the volume, thereby creating an electrical field having characteristics that are dependent at least in part on a moisture content of the volume. Another of the probes operates as a receiver probe for sensing the electrical field and producing an output signal having an output property that is dependent at least in part on the source signal and the moisture content within the volume. Means are provided for producing a moisture content value for the volume, where the moisture content value is based at least in part on the output property of the output signal.

20 Claims, 1 Drawing Sheet

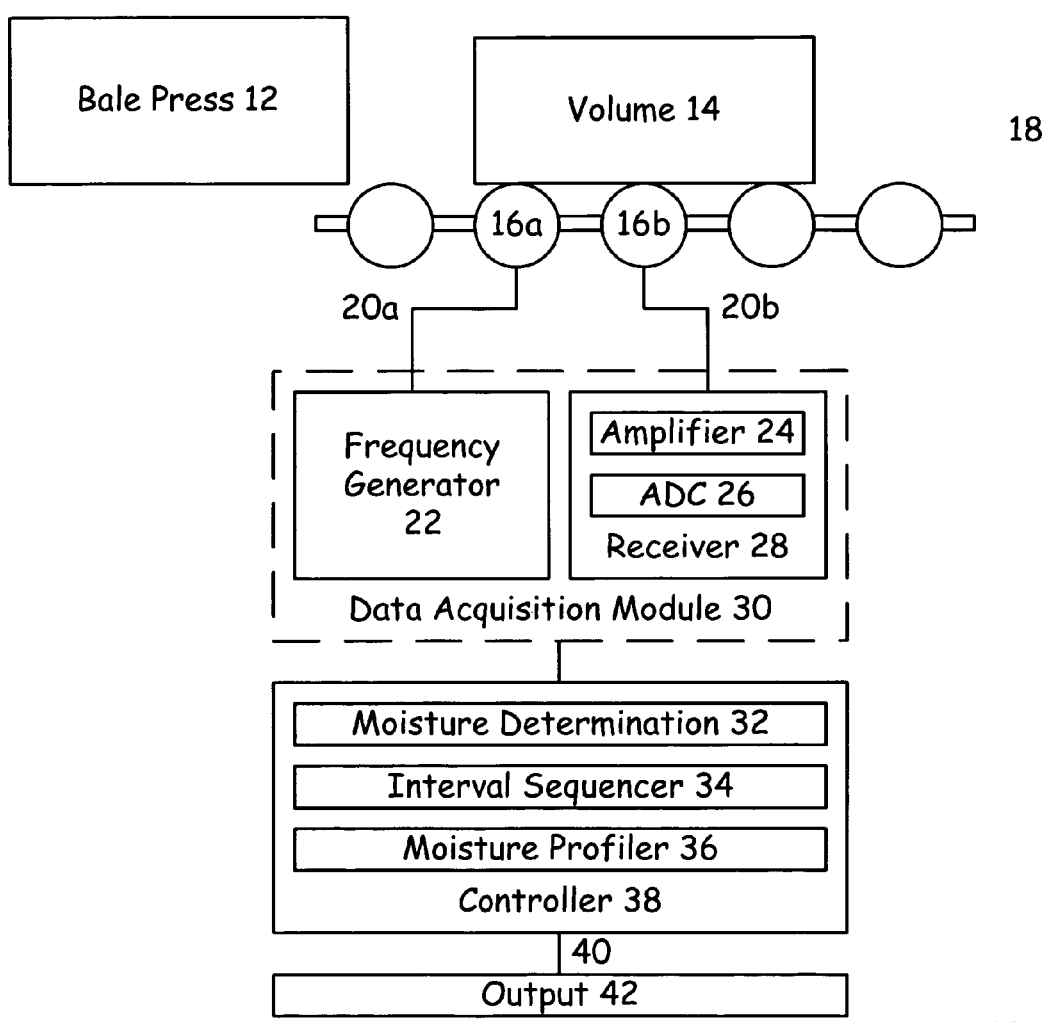

ULTRA LOW FREQUENCY MOISTURE SENSOR

FIELD

This invention relates to the field of moisture sensing. More particularly, this invention relates to determining the moisture content of cotton fibers in bales.

BACKGROUND

The moisture content of cotton fibers as they are processed through either a cotton gin or a cotton mill is preferably monitored and controlled. The amount of moisture within the cotton tends to have a great influence on various qualities of the cotton as it is processed. For example, the cotton fibers tend to break more readily if the moisture content drops too far during processing. As the cotton fibers during such processing are often carried along in air streams and subjected to heat, the moisture content can easily drop and the quality of the cotton fibers can easily be degraded if sufficient care is not taken to avoid such occurrences.

There are many places during such processing where it is desirable to take moisture readings on the cotton fibers. For example, moisture sensors have been developed to capture and sense the moisture in airborne fibers as they flow through the cotton gin. Another place where moisture readings are often taken is near the end of the ginning process, in order to determine the final moisture content of the bale. One place for measuring the cotton moisture content for the bale is where the cotton fibers are formed into bales in a tramper, prior to being strapped in a bale press and optionally wrapped. Moisture sensors have been developed to measure moisture by pressing into the cotton fibers while the cotton is being tramped to prepare it for being pressed into a bale.

The moisture sensors as described above are generally devices that function by measuring the electrical resistance between two or more electrodes. For the tramper moisture sensor, the electrodes are typically driven into a mass of the cotton fibers, and a current is run between the electrodes through the cotton mass. The moisture content of the fiber mass is determined by a correlation with one or more properties of the electrical resistance that is measured between the electrodes that penetrate the fiber mass.

However, there tend to be problems associated with such tramper moisture sensors for determining final bale moisture. One problem, for example, is that if the cotton fibers are sprayed with water for moisture restoration prior to exiting the tramper, the cotton fibers tend to become entangled and retained to some degree in the electrodes. Thus, the moisture readings are influenced, at least in part, by the same mass of fibers from reading to reading, until the retained fiber mass is removed from the electrodes.

What is needed, therefore, is a system by which moisture content readings can be taken on a large volume, such as a cotton bale, where the moisture sensor is not clogged by material from the volume, and where the readings tend to be more representative of the overall moisture content of the volume.

SUMMARY

The above and other needs are met by an apparatus for measuring a moisture content value within a volume. A frequency generator generates at least one source signal at frequencies of no more than about one kilohertz. Probes are preferably covered with an insulating material and are disposed with surfaces in physical contact with the volume, where no current flows between the probes through the volume. One of the probes is electrically connected to the frequency generator as a source probe, and adapted to receive the source signal and emit the source signal into the volume, thereby creating an electrical field having characteristics that are influenced at least in part by a moisture content of the volume. This electric field pattern preferably extends into the bulk of the volume. Another of the probes operates as a receiver probe for sensing the electrical field and producing an output signal having an output property that is dependent at least in part on the source signal and the moisture content within the volume. Means are provided for producing a moisture content value for the volume, where the moisture content value is based at least in part on the output property of the output signal.

In this manner, the moisture sensor of the present invention provides moisture readings that are more representative of the volume, rather than of just a small surface portion of the volume. Further, the probes of the present invention do not need to physically penetrate into the volume being measured, and thus the problems associated with fiber capture and retention in traditional electrodes are reduced or eliminated. For example, because the fiber retention problems are reduced, the same fiber mass does not influence the moisture readings over and over again, and the probes do not require the same routine maintenance and cleaning as traditional electrodes.

In various preferred embodiments, the volume is a cotton bale, which may be at least one of strapped and wrapped. The apparatus is preferably disposed at an outlet of a cotton gin, such as at the outlet of the cotton bale press, or at the input of a cotton mill, such as the lay down area, or in some other area. The probes are preferably formed as rollers across or under which the volume rolls. Preferably, the surfaces of the probes are non electrically conductive. In some embodiments the probes are disposed on a common surface face of the volume. An amplifier preferably receives, filters, and amplifies the output signal, and an analog to digital converter preferably receives and digitizes the output signal, prior to using the output signal to produce the moisture content value. The output property of the output signal is preferably an amplitude of the output signal, and the amplitude of the output signal is preferably empirically correlated with moisture content.

In some embodiments, the frequency source generates more than one source signal, where a first source signal having a lowest frequency is used for determining the moisture content value, and at least one second source signal having a higher frequency is used for distinguishing confounding variables. Preferably, only a single source signal having a frequency of about six hundred hertz is used. The signal source in some embodiments has an output potential of about forty volts, and in another about ten volts. Means are preferably provided for sampling the moisture content value of the volume at desired intervals. Preferably, the desired intervals are regularly repeating intervals. In various embodiments, the desired intervals are at least one of time intervals and distance intervals along the volume. Means are preferably provided for producing a moisture content profile of the volume from the moisture content values that are sampled at the desired intervals.

According to another aspect of the invention there is described an apparatus for measuring a moisture content value within a cotton bale. A frequency generator generates a source signal at a frequency of about six hundred hertz. A set of two probes physically contacts the cotton bale. The probes are disposed as rollers upon or under which the cotton bale rolls as it exits a cotton bale press. The probes thereby make contact with a common surface face of the cotton bale, and no direct current flows between the probes through the cotton bale. One probe from the set of two probes is electrically connected to the frequency generator as a source probe for receiving the source signal, and emitting the source signal into the volume, thereby creating an electrical field having characteristics that are dependent at least in part on a moisture content of the volume. Another probe from the set of two probes operates as a receiver probe for sensing the electrical field and producing an output signal having an amplitude that is dependent at least in part on the source signal and the moisture content within the cotton bale.

An amplifier receives and amplifies the source signal, and an analog to digital converter receives and digitizes the source signal. Means are provided for producing the moisture content value for the cotton bale, where the moisture content value is based at least in part on the amplitude of the output signal. Means are also provided for sampling the moisture content value of the cotton bale at multiple desired regular distance intervals along a length of the cotton bale. Means are used for producing a moisture content profile of the cotton bale from the moisture content values that are sampled at the desired intervals.

According to yet another aspect of the invention there is described a method for measuring a moisture content value within a cotton bale. A source signal is generated with a frequency generator at a frequency of about six hundred hertz. The cotton bale is physically contacted with a set of two probes, where the probes are disposed as rollers along which the cotton bale rolls as it exits a cotton bale press. The probes thereby make contact with a common surface face of the cotton bale, and no current flows between the probes through the cotton bale. One probe from the set of two probes is electrically connected to the frequency generator as a source probe for receiving the source signal, and emitting the source signal into the volume and thereby creating an electrical field having characteristics that are dependent at least in part on a moisture content of the volume.

Another probe from the set of two probes is operated as a receiver probe for sensing the electrical field and producing an output signal having an amplitude that is dependent at least in part on the source signal and the moisture content within the cotton bale. The output signal is received and amplified with an amplifier, and received and digitized with an analog to digital converter. The moisture content value for the cotton bale is produced, where the moisture content value is based at least in part on the amplitude of the output signal. The moisture content value of the cotton bale is sampled at multiple desired regular distance intervals along a length of the cotton bale, and a moisture content profile of the cotton bale is produced from the moisture content values that are sampled at the desired intervals.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and which depicts a functional block diagram of an apparatus according to a preferred embodiment of the invention.

DETAILED DESCRIPTION

With reference now to the FIGURE, there is depicted a system 10 according to a preferred embodiment of the present invention. The system 10 preferably operates to determine the moisture content within a volume 14. The volume 14 is preferably a fiber bundle, and most preferably a cotton bale 14, such as is typically formed in a bale press 12, such as is commonly disposed at the outlet of a cotton gin. The system 10 is preferably configured so as to determine the moisture content of a cotton bale 14 whether it is wrapped or unwrapped, strapped or unstrapped, and regardless of the orientation of the cotton bale 14. However, it is appreciated that the system 10 is also operable to determine the moisture content of a volume 14 that is not a cotton bale.

The system 10 preferably uses probes 16 to sense characteristics of the volume 14 that are dependent at least in part on the moisture content within the volume 14. In a most preferred embodiment, the probes 16 are disposed within a conveyor track 18, upon which the volume 14 is transported. For example, the probes 16 are in one embodiment configured as rollers 16 in a roller track 18, along which a cotton bale 14 travels as it exits a bale press 12. Thus, the probes 16 preferably do not penetrate the volume 14 to any significant degree.

Most preferably, the probes 16 are disposed such that at least one of their surfaces is in physical contact with the volume 14, although direct electrical contact is not necessary. Thus, the surfaces of the probes 16 that make physical contact with the volume 14 can be formed of either electrically conductive material, or non electrically conductive material, but in either case, there is preferably no direct current flowing from one probe 16a to another probe 16b through the volume 14. Interior portions of the probes 16 are preferably formed of electrically conductive materials, as described in more detail below.

In the embodiment where the probes 16 are formed as rollers 16, the outside surface of the probes 16 rotates as the volume 14 travels along the track 18. Thus, substantially all of the outer surface of the probes 16 in such embodiments makes repeated physical contact with the volume 14 at one time or another as the rollers 16 rotate under the volume 14 as it travels. In such a configuration, the rollers 16 could be initially formed with a non electrically conductive surface, such as being rubber coated, painted, anodized, or powder coated. However, with use over time, such a non electrically conductive coating tends to wear away, and the electrically conductive portions of the probes 16 may be exposed and come into contact with the volume 14. While this is acceptable, it is appreciated that the exterior surface of the probes 16 that contact the volume 14 need not be electrically conductive, and non electrically conductive surfaces tend to have some advantages, such as resistance to corrosion.

The probes 16 preferably contact just a single surface face of the volume 14, or in other words, are disposed so that they contact only one side of a cotton bale 14 as it rolls along the track 18. However, in alternate embodiments one or more of the probes 16 can be disposed on adjacent, opposite, or other such sides of the volume 14, depending upon the shape of the volume 14 or other factors.

There are most preferably two probes 16. However, in various embodiments a greater number of probes 16 can be used, which additional probes 16 can be disposed in the same track 18 configuration as depicted in the FIGURE, or can be disposed so as to contact other surface faces of the volume 14. Such additional probes 16 can be configured to work either as part of the same system 10 with the first two probes 16, or as part of additional systems. The probes 16 are most preferably electrically isolated from any structure such as the track 18 in which they may be mounted.

In one embodiment, the probes 16 are configured so that they make intermittent electrical contact with the leads 20 to which they are connected. This can be accomplished, for example, by placing one or more electrically conductive elements on the end of the probes 16, which elements make intermittent electrical contact with electrically conductive pickups as the elements rotate past the pickups while the rollers 16 rotate under the cotton bale 14 as it travels along the track 18. Of course, other methods of intermittent electrical contact are also contemplated within the present invention.

One of the probes 16a is electrically connected by an electrically conductive lead 20a to a frequency generator 22. The frequency generator 22 preferably produces at least one source signal, all of which source signals are preferably created at frequencies that are no greater than about one kilohertz. In a most preferred embodiment, only a single source signal is created, and the single source signal is created at a frequency of about six hundred hertz. Such ultra low frequencies, of less than about one kilohertz, are preferred over higher frequencies because they do not emit the damaging or otherwise dangerous radiation that may be present at higher frequencies, and yet it has been found that such ultra low frequencies are suitable for the uses described herein. Further, signals at such ultra low frequencies have been found to have relatively stable and relatively predictable correlations with moisture content, as describe in more detail below.

The source probe 16a preferably emits the source signal in to the volume 14 without passing any current into the volume 14. The source signal emitted into the volume 14 creates an electrical field that is disposed at least partially within the volume 14. Various characteristics of the volume 14, such as moisture content, tend to influence various characteristics of the electrical field that is set up by the source signal within the volume 14. Another probe 16b is preferably configured as a receiver probe 16b, which senses characteristics of the electrical field, such as those characteristics that are effected by the moisture content within the volume 14. The receiver probe 16b produces an output signal that is preferably conducted on an electrically conductive lead 20b to a receiver 28.

The receiver 28 most preferably includes an amplifier 24, which boosts and filters the output signal received from the receiver probe 16b. Preferably also included in the receiver 28 is an analog to digital converter 26, which converts the analog, and preferably amplified, output signal to a digital signal for analysis. However, it is appreciated that all of the manipulation and investigation of the output signal as described herein could also be performed in the analog domain, and need not be performed in the digital domain. However, the ubiquitous nature of computers tends to make digital signals easier to work with in the modern world.

In one embodiment the frequency generator 22 and the receiver 28 are part of a data acquisition module 30, such as a SOUND BLASTER type sound card that resides in a personal computer. In such configurations it is preferable that the sound card 30 be a full duplex sound card 30, so that the frequency generator 22 and the receiver 28 can operate simultaneously, which simultaneous operation is a preferred embodiment of the invention. In another embodiment, the data acquisition module 30 is part of a custom digital signal processor with an embedded microcomputer.

The output signal is preferably sent to a controller 38 for analysis. In various embodiments, the controller is preferably implanted in software, such as a program running on a personal computer in which the data acquisition module 30 is disposed. Alternately, the equipment as described herein can be embodied in dedicated hardware.

The output signal is preferably used to determine a moisture content value for the volume 14, such as with a moisture determination routine 32. In the preferred embodiment this is done by comparing one or more characteristic of the output signal to a table of output signal characteristics that have been sensed from systems with known independent variables. For example, to compute such a table, input signals at various known frequencies are generated and electrical fields are established in volumes 14 having known moisture contents, and perhaps other known characteristics. Various characteristics of the output signals created by the various combinations of the input signals and moisture contents are sensed and compiled into a table in association with the frequencies and moisture contents by which they were generated.

This table is then used to determine the moisture content of the volume 14 in the following manner. A source signal is generated at a known frequency and the source probe 16a is used to set up an electrical field within the volume 14, where the volume 14 has an unknown moisture content. The electrical field is sensed with the receiver probe 16b, and the output signal is processed as describe above. The desired characteristics of the output signal are then compared to the corresponding characteristics as listed in the table for source signals of the same frequency. The moisture content data in the table is either interpolated or regressed to determine a moisture content value for the unknown volume 14. In a most preferred embodiment, the characteristic of the output signal that is used to determine the moisture content value of the volume 14 is the peak to peak amplitude of the output signal.

The controller 38 preferably includes an interval sequencer 34 of some type, so that the output signal can be sampled at intervals. The intervals are preferably regularly spaced intervals, where the intervals are at least one of time intervals or distance intervals along the length of the volume 14 as it passes across the probes 16. One method of creating sampling intervals has been described above, in regard to using intermittent contacts on the rolling probes 16. It is appreciated that such mechanical methods can be either augmented or replaced by logical methods constructed within the controller 38, and that all combinations and methods of such are contemplated within the present invention.

When such interval sequencing is available, the system 10 also preferably includes a moisture profiler 36, which creates a moisture profile for the volume 14. In other words, instead of taking just a single moisture reading on the volume 14, the system 10 preferably takes multiple moisture readings on the volume 14, and most preferably uses the multiple moisture readings to create a moisture profile for the volume 14. The moisture profile preferably includes information such as a graphical depiction of the volume 14 with a trend chart of the moisture content value at different positions within the volume 14, such as along the length of the volume 14. Alternately, the moisture content profile depicts how the moisture content distribution within the volume 14 changes over time, if the volume 14 either remains in physical contact with the probes 16, or is repeatedly brought back over time to make physical contact with the probes 16.

This may be of use to cotton merchants to see the change in moisture content from when they purchased the bale to when they sell the bale. It may also be of interest to textile mills to see the moisture content when they purchase the bale and put it into their warehouse and when they take the bale from the warehouse to the spinning mill for processing. Thus, there are many different embodiments for the moisture profile that could be created as contemplated by the present invention.

The moisture content values, whether they be single values or multiple moisture content values in a moisture profile, are preferably sent out of the controller 38 by a connection 40 to an output 42. The output 42 can take many different forms in various embodiments, such as, by way of example and not limitation, a data storage device, a display, an alarm system, an interlock, or a remote computing device. It is appreciated that all or any portion of the other data as described above can also be sent to the output 42, in addition to the moisture content values.

Thus, the system 10 as described herein is operable to determine a moisture content within a volume 14. Most preferably the moisture that is sensed is water moisture. However, in alternate embodiments the moisture that is sensed is any liquid, such as alcohol or water with various impurities, such as various concentrations of salt or other minerals. Tables or algorithms for the correlation of such various liquids can be compiled so that they can be sensed and reported, even when different ones of such liquids coexist within the same volume 14.

In some embodiments the frequency generator 22 produces more than one source signal. However, in all such embodiments, the fundamental source signals produced are at a frequency that is less than about one kilohertz. Also, in all such embodiments, the source signal having the lowest frequency is the source signal that is used to determine the moisture content within the volume 14, and the other source signals having higher frequencies are preferably used to reduce confounding variables within the data.

The source signal is preferably created at a potential of between about ten volts and about forty volts. However, this potential is dependent on a variety of factors, such as the surface area of the probes, the distance between the probes, the mass of the volume 14, and the composition of the volume 14. When the volume 14 is a cotton bale of standard dimensions, and the source signal has a frequency of about six hundred hertz, and the probes 16 are configured as rollers with a diameter of about two inches, and a length of about three feet, and are disposed at a distance of no more than about a half inch from one another, the potential of forty volts works quite well when using a sound card as the data acquisition module 30. However, when using an embedded controller, a potential of about ten volts works well.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for measuring a moisture content value within a volume comprising a fiber bale, the apparatus comprising:
   a frequency generator adapted to generate at least one source signal at a fundamental frequency of no more than about one kilohertz,
   probes disposed with surfaces in physical contact with the volume, where no current flows between the probes through the volume,
   one of the probes electrically connected to the frequency generator as a source probe, and adapted to receive the source signal and emit the source signal into the volume, thereby creating an electrical field having characteristics that are dependent at least in part on a moisture content of the volume,
   another of the probes operating as a receiver probe for sensing the electrical field and producing an output signal having an output property that is dependent at least in part on the source signal and the moisture content within the volume, and
   means for producing a moisture content value for the volume, where the moisture content value is based at least in part on the output property of the output signal.

2. The apparatus of claim 1, wherein the volume is a cotton bale.

3. The apparatus of claim 1, wherein the volume is a cotton bale that is strapped and wrapped.

4. The apparatus of claim 1, wherein the apparatus is disposed at one of an outlet of a cotton bale press and the input to a cotton mill.

5. The apparatus of claim 1, wherein the probes are formed as rollers against which the volume rolls.

6. The apparatus of claim 1, wherein the surfaces of the probes are non electrically conductive.

7. The apparatus of claim 1, wherein the probes are disposed on a common surface face of the volume.

8. The apparatus of claim 1, further comprising an amplifier for receiving the output signal and amplifying and filtering the output signal prior to using the output signal to produce the moisture content value.

9. The apparatus of claim 1, further comprising an analog to digital converter for receiving the output signal and digitizing the output signal prior to using the output signal to produce the moisture content value.

10. The apparatus of claim 1, wherein the output property of the output signal is an amplitude of the output signal, and the amplitude of the output signal is empirically correlated with moisture content.

11. The apparatus of claim 1, wherein the frequency source generates more than one source signal, where a first source signal having a lowest frequency is used for determining the moisture content value, and at least one second source signal having a higher frequency is used for distinguishing confounding variables.

12. The apparatus of claim 1, wherein the signal source has an output potential of from about ten volts to about forty volts.

13. The apparatus of claim 1, wherein only a single source signal having a frequency of about six hundred hertz is used.

14. The apparatus of claim 1, further comprising means for sampling the moisture content value of the volume at desired intervals.

15. The apparatus of claim 14, wherein the desired intervals are regularly repeating intervals.

16. The apparatus of claim 14, wherein the desired intervals are time intervals.

17. The apparatus of claim 14, wherein the desired intervals are distance intervals along the volume.

18. The apparatus of claim 14, further comprising means for producing a moisture content profile of the volume from the moisture content values that are sampled at the desired intervals.

19. An apparatus for measuring a moisture content value within a cotton bale, the apparatus comprising:
   a frequency generator for generating a source signal at a frequency of less than about one kilohertz,
   a set of two probes physically contacting the cotton bale, the probes disposed as rollers against which the cotton bale rolls as it exits a cotton bale press, the probes thereby making contact with a common surface face of the cotton bale, and where no current flows between the probes through the cotton bale,
   one probe from the set of two probes electrically connected to the frequency generator as a source probe for receiving the source signal, and emitting the source signal into the volume, thereby creating an electrical field having characteristics that are dependent at least in part on a moisture content of the volume,
   another probe from the set of two probes operating as a receiver probe for sensing the electrical field and producing an output signal having an amplitude that is dependent at least in part on the source signal and the moisture content within the cotton bale,
   an amplifier for receiving the source signal and amplifying and filtering the source signal,
   an analog to digital converter for receiving the source signal and digitizing the source signal,
   means for producing the moisture content value for the cotton bale, where the moisture content value is based at least in part on the amplitude of the output signal,
   means for sampling the moisture content value of the cotton bale at multiple desired regular distance intervals along a length of the cotton bale, and
   means for producing a moisture content profile of the cotton bale from the moisture content values that are sampled at the desired intervals.

20. A method for measuring a moisture content value within a cotton bale, the method comprising the steps of:
   generating a source signal with a frequency generator at a frequency of about six hundred hertz,
   physically contacting the cotton bale with a set of two probes, the probes disposed as rollers along which the cotton bale rolls as it exits a cotton bale press, the probes thereby making contact with a common surface face of the cotton bale, and where no current flows between the probes through the cotton bale,
   electrically connecting one probe from the set of two probes to the frequency generator as a source probe for receiving the source signal,
   emitting the source signal into the volume and thereby creating an electrical field having characteristics that are dependent at least in part on a moisture content of the volume,
   operating another probe from the set of two probes as a receiver probe for sensing the electrical field and producing an output signal having an amplitude that is dependent at least in part on the source signal and the moisture content within the cotton bale,
   receiving the output signal and amplifying and filtering the output signal with an amplifier,
   receiving the output signal and digitizing the output signal with an analog to digital converter,
   producing the moisture content value for the cotton bale, where the moisture content value is based at least in part on the amplitude of the output signal,
   sampling the moisture content value of the cotton bale at multiple desired regular distance intervals along a length of the cotton bale, and
   producing a moisture content profile of the cotton bale from the moisture content values that are sampled at the desired intervals.

* * * * *